(12) United States Patent
Ko et al.

(10) Patent No.: US 10,756,719 B2
(45) Date of Patent: Aug. 25, 2020

(54) ANALOG SWITCH FOR TRANSMITTING HIGH VOLTAGE SIGNALS WITHOUT UTILIZING HIGH VOLTAGE POWER SUPPLIES

(71) Applicant: Microchip Technology Inc., Chandler, AZ (US)

(72) Inventors: Isaac Ko, Kowloon (HK); Ka Wai Ho, Kowloon (HK); Wan Tim Chan, Yuen Long (HK); Jimes Lei, Milpitas, CA (US)

(73) Assignee: MICROCHIP TECHNOLOGY INC., Chandler, AZ (US)

( * ) Notice: Subject to any disclaimer, the term of this patent is extended or adjusted under 35 U.S.C. 154(b) by 1319 days.

(21) Appl. No.: 14/919,000

(22) Filed: Oct. 21, 2015

(65) Prior Publication Data

US 2016/0191036 A1 Jun. 30, 2016

(30) Foreign Application Priority Data

Dec. 31, 2014 (CN) .......................... 2014 1 0845913

(51) Int. Cl.
*H03K 17/693* (2006.01)
*H03K 17/06* (2006.01)
*A61B 8/00* (2006.01)

(52) U.S. Cl.
CPC ......... *H03K 17/063* (2013.01); *A61B 8/4444* (2013.01); *H03K 17/693* (2013.01); *H03K 2217/0009* (2013.01)

(58) Field of Classification Search
CPC ..... H03K 17/06; H03K 17/063; H03K 17/081
See application file for complete search history.

(56) References Cited

U.S. PATENT DOCUMENTS

| 8,451,044 | B2* | 5/2013 | Nisbet | H03K 17/687 |
|---|---|---|---|---|
| | | | | 327/308 |
| 9,401,659 | B2* | 7/2016 | Lei | H02M 7/217 |
| 9,531,368 | B2* | 12/2016 | Honda | H03K 17/063 |
| 2014/0112024 | A1 | 4/2014 | Lei et al. | |

FOREIGN PATENT DOCUMENTS

| CN | 1595801 | A | 3/2005 |
|---|---|---|---|
| CN | 101984517 | A | 3/2011 |
| CN | 103001206 | A | 3/2013 |
| CN | 103249216 | A | 8/2013 |

* cited by examiner

*Primary Examiner* — Hai L Nguyen
(74) *Attorney, Agent, or Firm* — DLA Piper LLP US

(57) ABSTRACT

Described herein are multiple designs for an improved analog switch for use in transmitting high voltage signals without using high voltage power supplies for the switch. The analog switches are able to pass and block input signals in the approximate range of −100V to +100V. The use of translinear loops and a bootstrap configuration results in a constant on-resistance of the symmetrical switches and matches the conductance of each analog switch to the transconductance of an NMOS transistor, which can be easily stabilized with a constant $g_m$ biasing scheme. In certain embodiments, a shunt termination (T-switch) configuration is used for better off-isolation, and each of the symmetrical switches has its own translinear loop and thus flexibility of on-resistance and termination voltage.

5 Claims, 7 Drawing Sheets

ANALOG SWITCH FOR TRANSMITTING HIGH VOLTAGE SIGNALS WITHOUT UTILIZING HIGH VOLTAGE POWER SUPPLIES

TECHNICAL FIELD

Described herein are multiple designs for an improved analog switch for use in transmitting high voltage signals without using high voltage power supplies for the switch. The analog switches are able to pass and block input signals in the approximate range of −100V to +100V. The use of translinear loops and a bootstrap configuration results in a constant on-resistance of the symmetrical switches and matches the conductance of each analog switch to the transconductance of an NMOS transistor, which can be easily stabilized with a constant $g_m$ biasing scheme. In certain embodiments, a shunt termination (T-switch) configuration is used for better off-isolation, and each of the symmetrical switches has its own translinear loop and thus flexibility of on-resistance and termination voltage.

BACKGROUND OF THE INVENTION

Numerous prior art devices require the use of an analog switch that can pass or block a high voltage input signal. An example of such a device is depicted in FIG. 1. Medical ultrasound system 100 comprises a plurality of probes, here labeled as exemplary probes 131, 132, 133, and 134. Additional probes may be utilized. Each probe is coupled to one or more sets of an analog switch and transducer. In this example, probe 131 is coupled to analog switches 111, 112, 113, and 114, each of which receives high voltage input signal 140 from probe 131. Analog switch 111 is coupled to transducer 121, analog switch 112 is coupled to transducer 122, analog switch 113 is coupled to transducer 123, and analog switch 114 is coupled to transducer 124 Additional sets of an analog switch and transducer can be utilized. The role of each of the analog switches 111, 112, 113, and 114 is to connect or disconnect the probe (such as probe 131) to the switch's respective transducer.

An example of a prior art analog switch is shown in FIG. 2. Analog switch 111 receives high voltage input signal 140, which in this example ranges from +100V to −100V. Analog switch 111 comprises transistors 211, 212, 240, 261, and 262 as depicted. Transistors 261 and 262 receive control signal 270. Control signal 270 turns analog switch 111 on or off. When control signal 270 is low, transistor 261 (which is a PMOS transistor) turns on and its drain is pulled to $V_{PP}$ (which here is +100V), and transistor 262 (which is an NMOS transistor) turns off. When control signal 270 is high, transistor 261 turns off, and transistor 262 turns on and its drain is pulled down to $V_{NN}$ (which here is −100V).

The drain of transistor 261 and the drain of transistor 262 form a node that connects to the gates of transistors 211 and 212. When control signal 270 is low, transistors 211 and 212 will turn on, which will allow high voltage input signal 140 to be sent to transducer 121.

When control signal 270 is high, transistors 211 and 212 will turn off. Control signal 270 will turn on transistor 240, which will pull the node between transistors 211 and 212 down to $V_{NN}$ (which is −100V). Transistor 240 provides a shunt termination function and improves the off-isolation of switch 111. Notably, however, transistor 240 requires a high-voltage negative supply (here, $V_{NN}$=−100V).

There are numerous drawbacks with the prior art design of FIG. 2. First, it requires significant board space and has a complicated board design and layout, which results in high manufacturing costs. Second, the presence of high DC voltages (+/−100V) in the probe could cause a bad shock for the operator or patient. Third, the system requires a low-impedance, high-voltage power cord that is neither thin nor flexible. Fourth, a stringent power-up sequence must be followed to prevent transistor breakdown and latch-up. Fifth, the system requires the use of thick gate oxide and may not be feasible with nominal BCD (Bipolar-CMOS-DMOS) processes.

The prior art includes one attempted solution. FIG. 3 depicts analog switch 300. Under this design, the positive high voltage supply can be lowered down to 5V instead of 100V if transistors 310 and 320 are low threshold transistors and their gates are clamped to their sources with zener diode 330. However, analog switch 300 still requires a high negative voltage (here, −100V) for the shunt termination function, which still causes the drawbacks described previously.

What is needed is an improved analog switch design that can transmit high voltages to a load without requiring high voltage DC power supplies.

SUMMARY OF THE INVENTION

The embodiments disclosed herein are improved analog switch designs that are able to transmit high voltage signals without using high voltage DC power supplies.

DETAILED DESCRIPTION OF THE PREFERRED EMBODIMENTS

Figure 4:
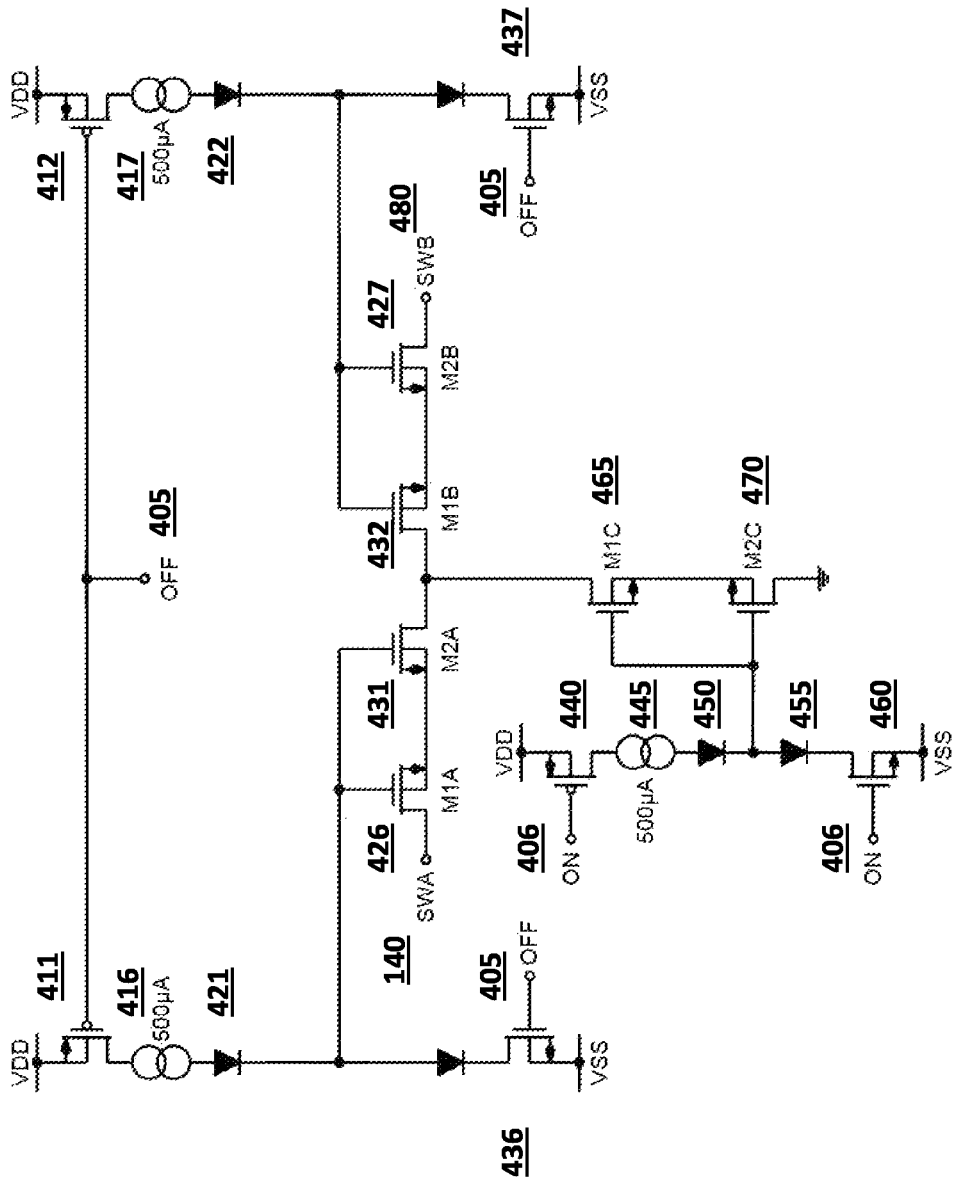
FIG. 4 depicts an embodiment of an analog switch.

FIG. 4 depicts analog switch 400. Analog switch 400 comprises a shunt that terminates to ground instead of to a high voltage negative power supply as in the prior art.

Analog switch 400 is controlled by control signal 405 and its inverse, control signal 406, and receives input signal 140 and generates output signal 480.

When control signal 405 is low and control signal 406 is high, transistors 411 and 412 (which both are PMOS transistors) are turned on and allow voltage $V_{DD}$ to pass through to the gates of transistors 426, 427, 431, and 432. Transistor 440 (which is a PMOS transistor) is turned off, and transistor 460 (which is an NMOS transistor) is turned on, which pulls the gates of transistors 465 and 470 to $V_{SS}$, which results in transistors 465 and 470 being turned off. The input signal 140 flows through transistors 426, 427, 431, and 432, and appears as output signal 427.

When control signal 405 is high and control signal 406 is low, transistors 411 and 412 are turned off and transistors 436 and 437 are turned on, which pulls the gates of transistors 426, 427, 431, and 432 to $V_{SS}$, which results in transistors 426, 427, 431, and 432 being turned off. Transistor 440 is turned on, transistor 460 is turned off, resulting in the gates of transistors 465 and 470 being pulled to $V_{DD}$, which results in transistors 465 and 470 being turned on, which in turn results in the node between transistors 431 and 432 being pulled to ground. This provides off-isolation. The end result is that the input signal 140 is blocked and does not appear as output signal 427, as analog switch 400 is off.

Figure 5:
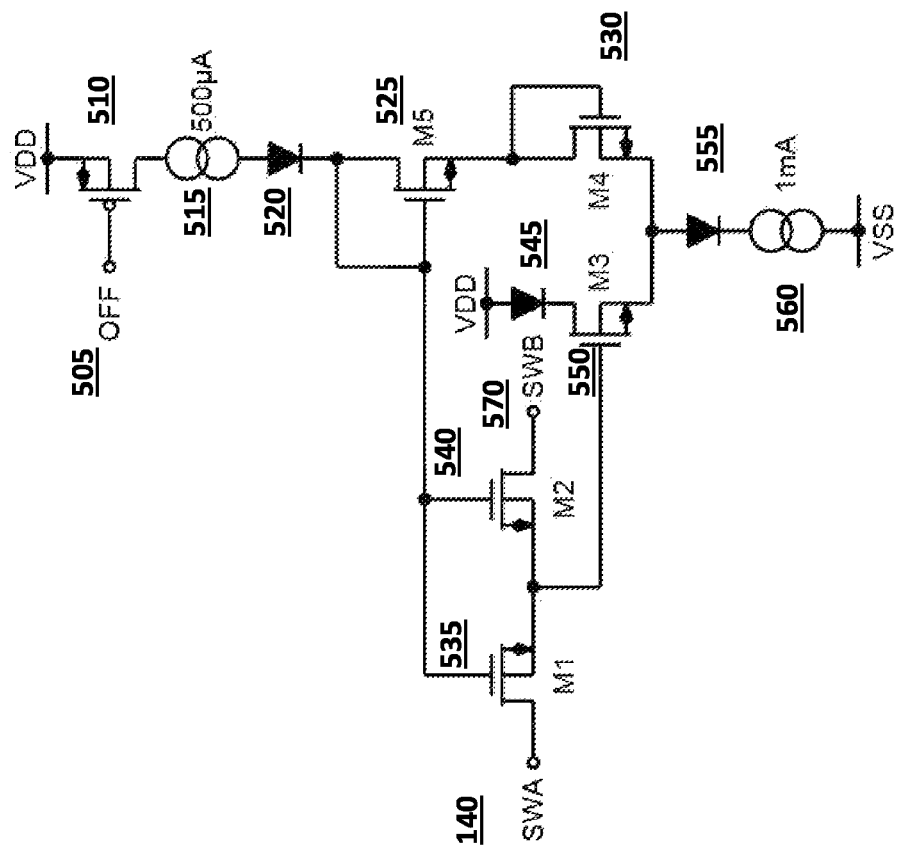
FIG. 5 depicts another embodiment of an analog switch.

Another embodiment is shown in FIG. 5. Analog switch 500 eliminates harmonic distortion and supply modulation through the use of translinear loops.

When control signal 505 is low, transistor 510 (which is a PMOS transistor) is turned on, which results in $V_{DD}$ being applied to the gates of transistor 525, 535, and 540, which each is turned on as a result. The input signal 140 propagates to output signal 570.

When control signal 505 is high, transistor 510 is turned off, and the gate of transistors 525, 535, and 540 are pulled down to $V_{SS}$ and are turned off. The input signal 140 is blocked from appearing as output signal 570.

In this embodiment, because $V_{GS}$ of transistor 535 and $V_{GS}$ of transistor 540=$V_{GS}$ of transistor 525, the conductance of transistors 535 and 540 equals the transconductance of transistor 525 and is independent of the input signal 140 and supply voltages $V_{DD}$ and $V_{SS}$. Thus, harmonic distortion and supply modulation are eliminated.

Figure 6:
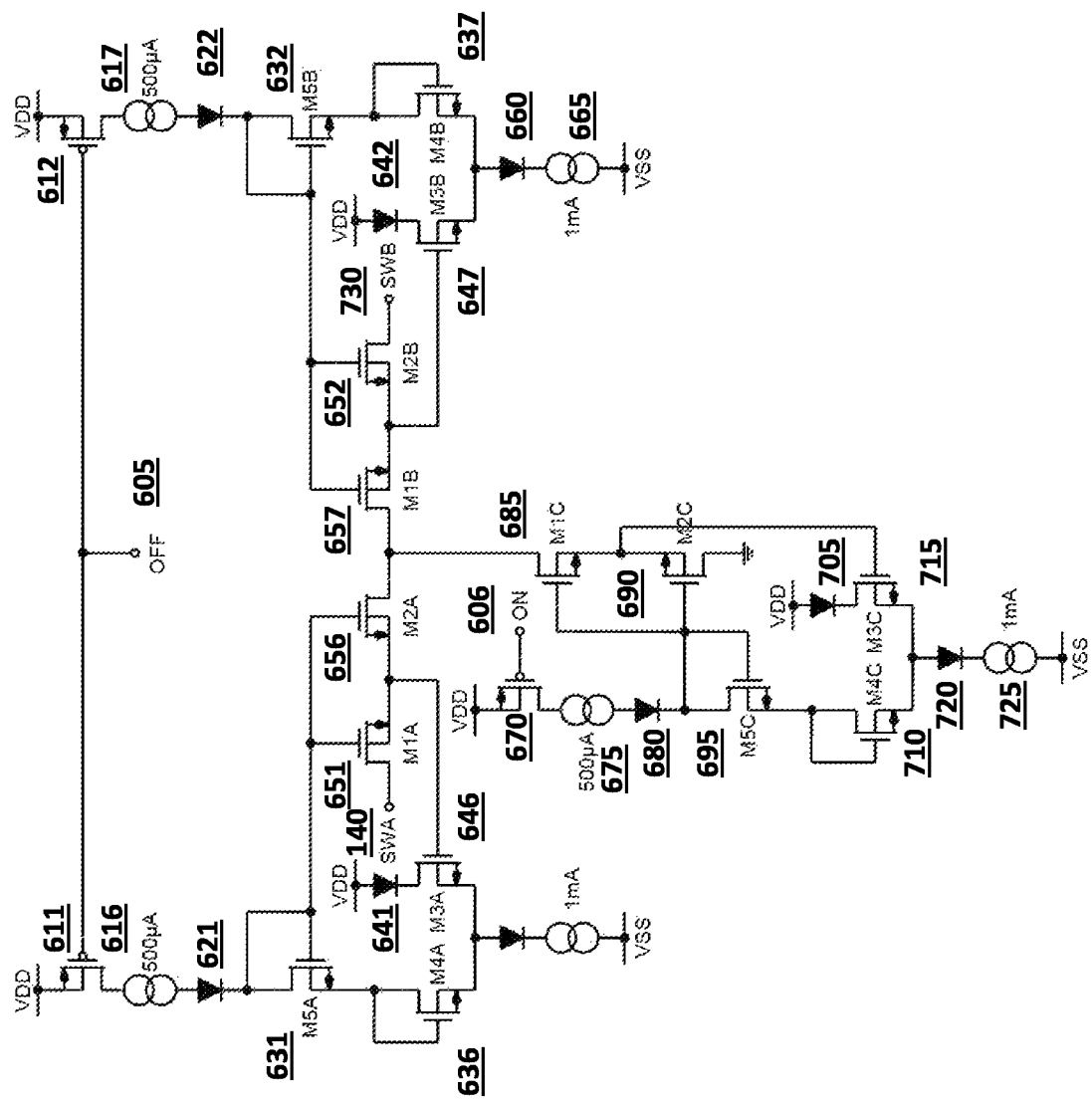
FIG. 6 depicts another embodiment of an analog switch.

Another embodiment is shown in FIG. 6 as analog switch 600. Analog switch 600 is controlled by control signal 605 and its inverse, control signal 606.

When control signal 605 is low and control signal 606 is high, transistors 611 and 612 (which are PMOS transistors) are turned on, and the gates of transistors 631, 632, 651, 652, 656, and 657 are pulled to $V_{DD}$ and those transistors are turned on. Input signal 140 propagates to output signal 730.

When control signal 605 is high and control signal 606 is low, transistors 611 and 612 are turned off, and the gates of transistors 631, 632, 651, 652, 656, and 657 are pulled to $V_{SS}$ and those transistors are turned off. Transistor 670 is turned on, and the gates of transistors 685 and 690 are pulled to $V_{DD}$ and those transistors are turned on, which pulls the node between transistors 656 and 657 to ground. This provides off-isolation but without a high voltage negative power supply.

Figure 1:
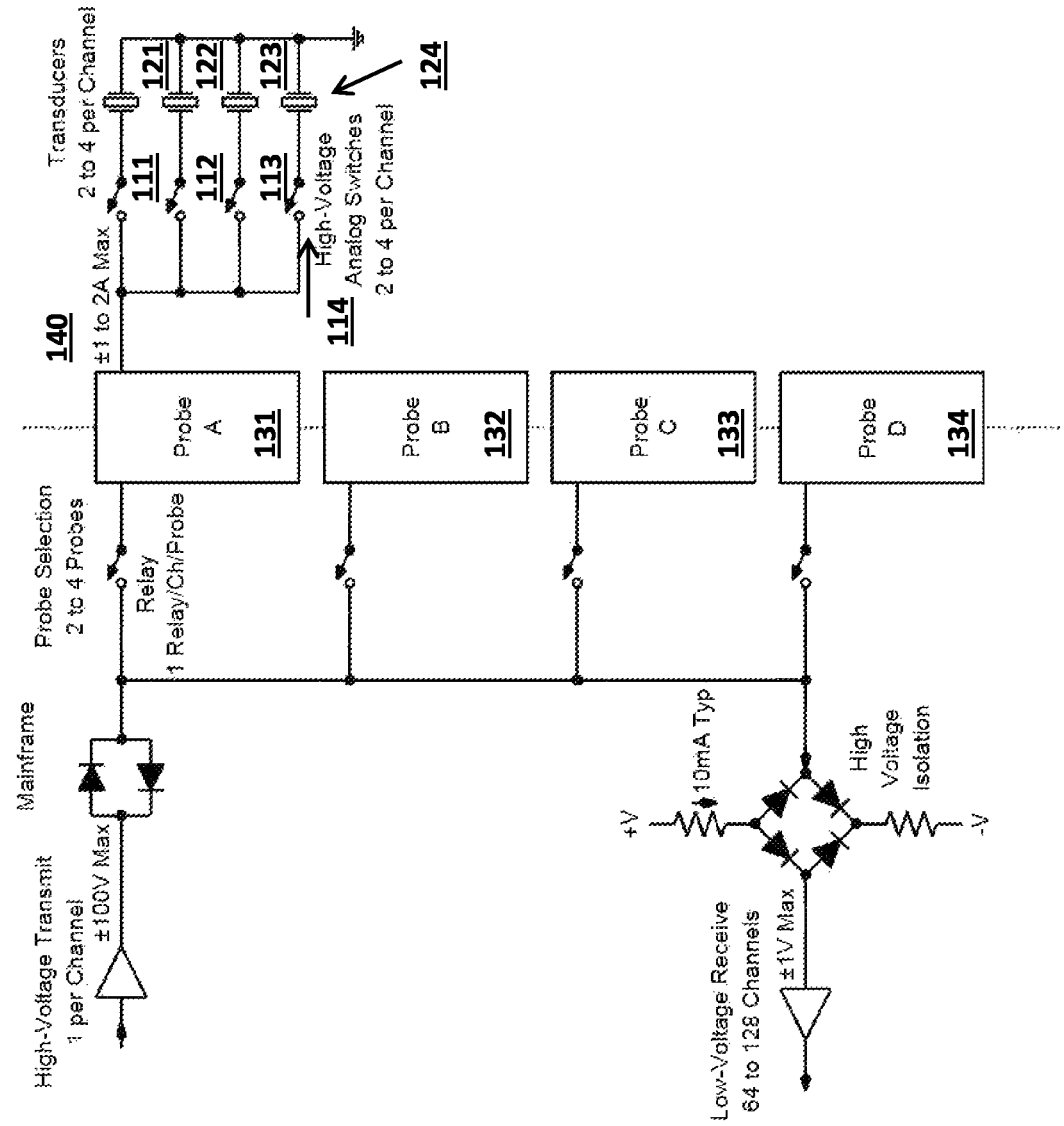
FIG. 1 depicts a prior art medical ultrasound device.
Figure 2:
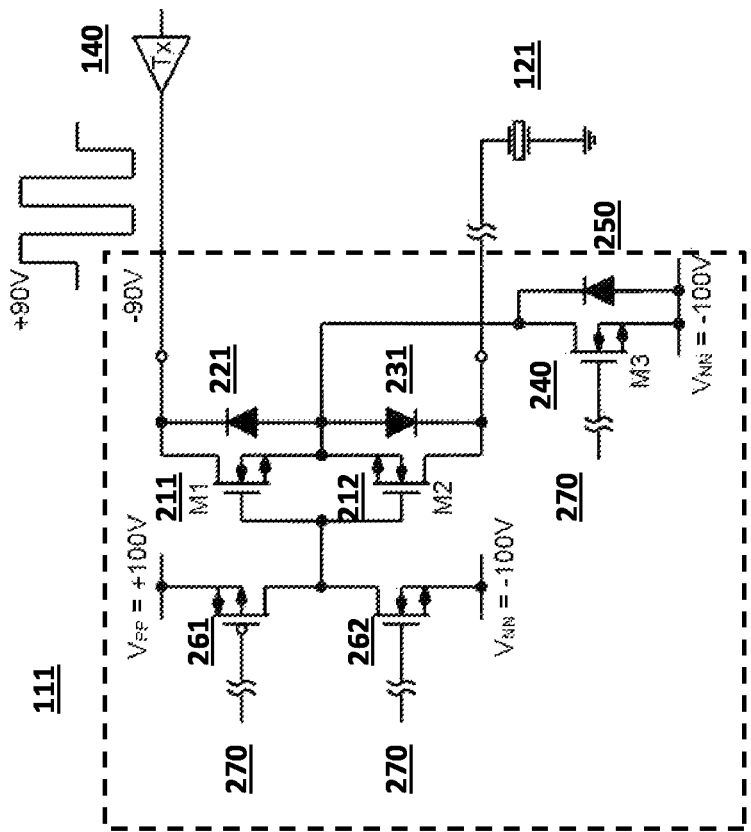
FIG. 2 depicts a prior art analog switch.
Figure 3:
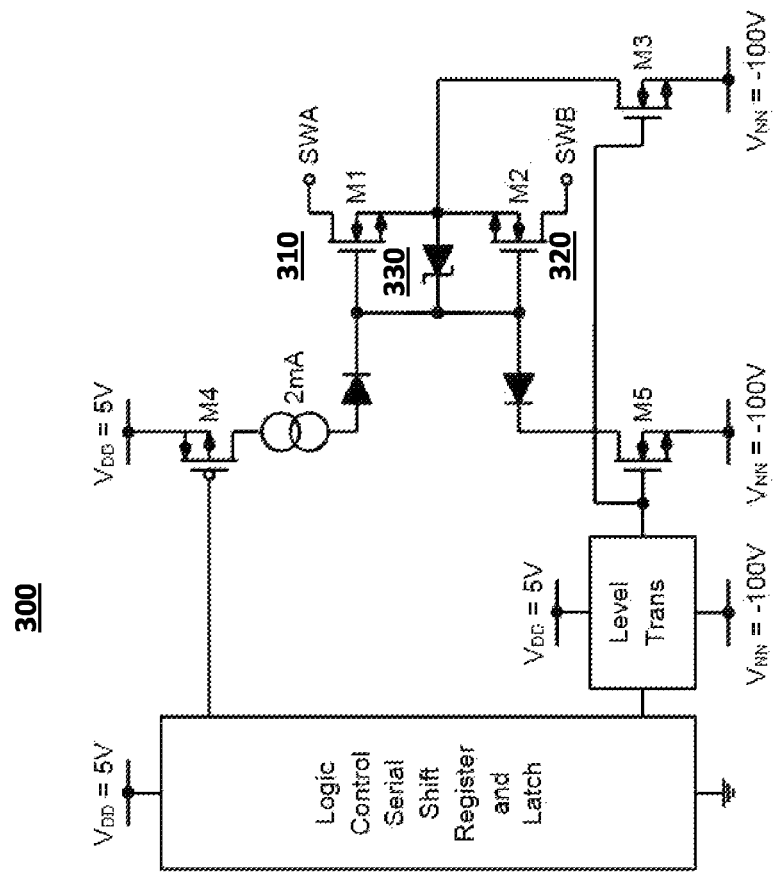
FIG. 3 depicts another prior art analog switch.
Figure 7:
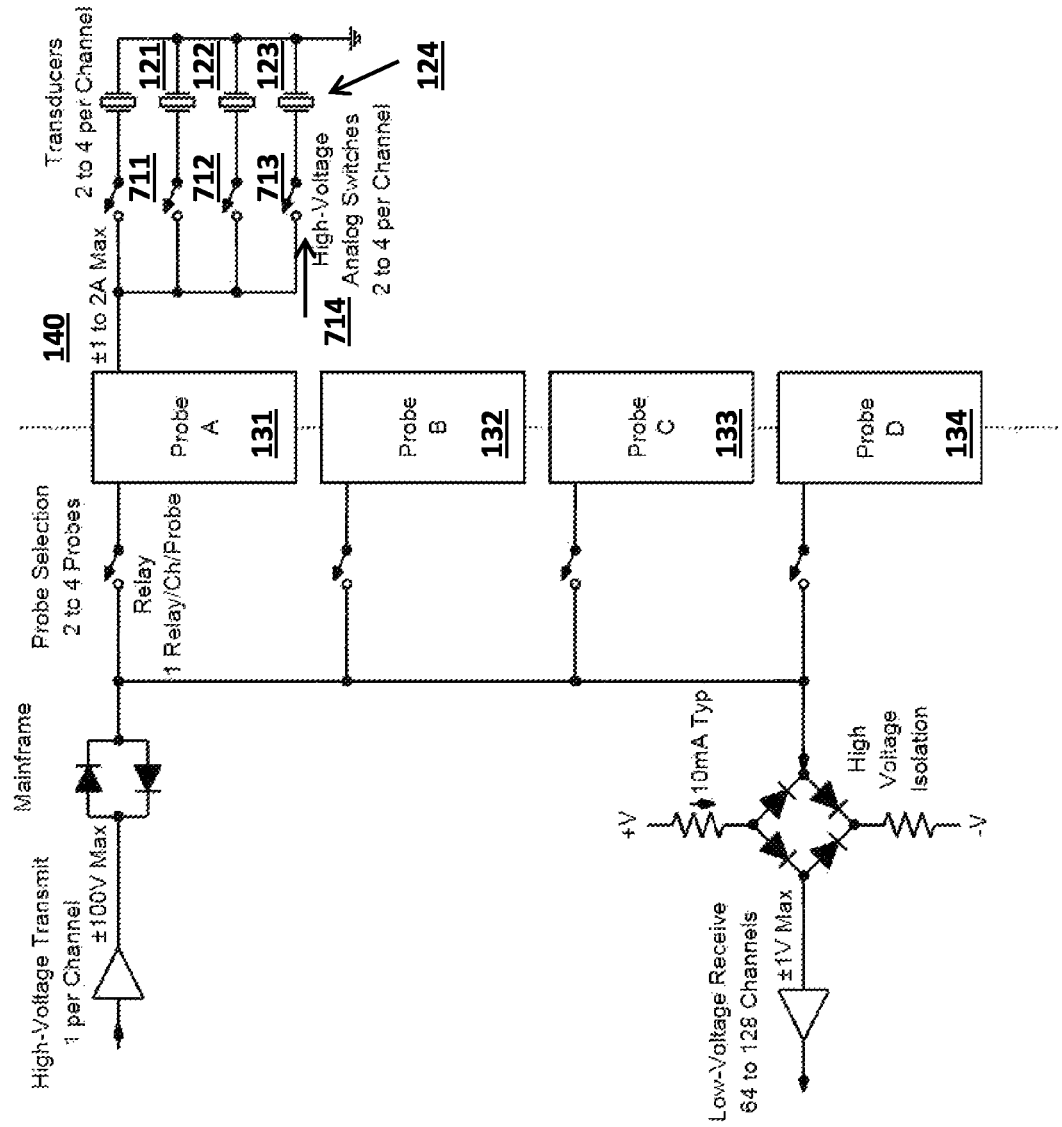
FIG. 7 depicts and embodiment of a medical ultrasound device.

The embodiments described above can be used to in devices, such as a medical ultrasound system, that require analog switches that can pass or block high voltage signals. FIG. 7 depicts medical ultrasound system 700. Medical ultrasound system 700 comprises a plurality of probes, here labeled as exemplary probes 131, 132, 133, and 134 as in FIG. 1. Additional probes may be utilized. Each probe is coupled to one or more sets of an analog switch and transducer. In this example, probe 131 is coupled to analog switches 711, 712, 713, and 714, each of which receives high voltage signal 140 from probe 131, and each of which is built according to the design of one of the embodiments described above with reference to FIGS. 4-6.

Analog switch 711 is coupled to transducer 121, analog switch 712 is coupled to transducer 122, analog switch 713 is coupled to transducer 123, and analog switch 714 is coupled to transducer 124 Additional sets of an analog switch and transducer can be utilized. The role of each of the analog switches 711, 712, 713, and 714 is to connect or disconnect the probe (such as probe 131) to the switch's respective transducer. Due to the design of analog switches 711, 712, 713, and 714, medical ultrasound system 700 is a significant improvement over the prior art medical ultrasound system 100 of FIG. 1.

The advantages of the embodiments described above are numerous. First, high voltage DC power supplies are not required or utilized, which eliminates the drawbacks of the prior art systems. Second, adding translinear loops makes the analog switch conductance constant, which eliminates harmonic distortion and supply modulation. Third, a nominal BCD process can be used, and no thick gate oxide devices are required, which increases the ease and decreases the cost of manufacturing.

References to the present invention herein are not intended to limit the scope of any claim or claim term, but instead merely make reference to one or more features that may be covered by one or more of the claims. Materials, processes and numerical examples described above are exemplary only, and should not be deemed to limit the claims. It should be noted that, as used herein, the terms "over" and "on" both inclusively include "directly on" (no intermediate materials, elements or space disposed there between) and "indirectly on" (intermediate materials, elements or space disposed there between).

What is claimed is:

1. An analog switch, comprising:
a first transistor comprising a first terminal, a second terminal, and a gate, wherein the first terminal is configured to receive a high voltage input signal and the gate receives a first voltage when a control signal is low and receives a second voltage when the control signal is high, wherein the magnitude of the first voltage and the magnitude of the second voltage are smaller than the magnitude of the high voltage input signal;
a second transistor comprising a first terminal, a second terminal, and a gate, wherein the first terminal of the second transistor is coupled directly or indirectly to the second terminal of the first transistor, the gate of the second transistor receives the first voltage when the control signal is low and receives the second voltage when the control signal is high, and the second terminal of the second transistor presents the high voltage input signal when the gate of the second transistor receives the first voltage and blocks the high voltage input signal when the gate of the second transistor receives the second voltage; and
a shunt circuit connected to a node between the first transistor and the second transistor, wherein the shunt circuit pulls the node to ground when the control signal is high, and wherein the shunt circuit is powered by the first voltage and the second voltage.

2. The analog switch of claim 1, wherein the high voltage input signal ranges between +100 volts and −100 volts.

3. The analog switch of claim 1, wherein the shunt circuit does not alter the voltage of the node between the first transistor and the second transistor when the when the control signal is low.

4. A medical ultrasound device, comprising:
a probe; and
a plurality of transducers, each transducer coupled to the probe through an analog switch;
wherein each analog switch comprises:
a first transistor comprising a first terminal, a second terminal, and a gate, wherein the first terminal is configured to receive a high voltage input signal and the gate receives a first voltage when a control signal is low and receives a second voltage when the control signal is high, wherein the magnitude of the first voltage and the magnitude of the second voltage are smaller than the magnitude of the high voltage input signal;
a second transistor comprising a first terminal, a second terminal, and a gate, wherein the first terminal of the second transistor is coupled directly or indirectly to the second terminal of the first transistor, the gate of the second transistor receives the first voltage when the control signal is low and receives the second voltage when the control signal is high and the second terminal of the second transistor presents the high voltage input signal when the gate of the second transistor receives the first voltage and blocks the high voltage input signal when the gate of the second transistor receives the second voltage; and a shunt circuit connected to a node between the first transistor and the second transistor, wherein the shunt circuit pulls the node to ground when the control signal is high and wherein the shunt circuit is powered by the first voltage and the second voltage.

5. The medical ultrasound device of claim 4, wherein the high voltage input signal ranges between +100 volts and −100 volts.

\* \* \* \* \*